United States Patent [19]

Förster et al.

[11] Patent Number: 5,328,897
[45] Date of Patent: * Jul. 12, 1994

[54] HERBICIDAL 2-(2-BENZOXAZOLYL-OXY)-ACETAMIDES

[75] Inventors: Heinz Förster, Wuppertal; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[ * ] Notice: The portion of the term of this patent subsequent to Nov. 15, 2005 has been disclaimed.

[21] Appl. No.: 956,127

[22] Filed: Oct. 2, 1992

[30] Foreign Application Priority Data

Oct. 11, 1991 [DE] Fed. Rep. of Germany ....... 4133673

[51] Int. Cl.⁵ ........................................... C07D 263/58
[52] U.S. Cl. ..................... 504/270; 548/221
[58] Field of Search ....................... 504/270; 548/221; 514/375

[56] References Cited

U.S. PATENT DOCUMENTS

| | | | |
|---|---|---|---|
| 4,384,881 | 5/1983 | Kuyama et al. | 548/171 |
| 4,408,055 | 10/1983 | Forster et al. | 504/270 |
| 4,456,466 | 6/1984 | Krass et al. | 504/270 |
| 4,465,504 | 8/1984 | Forster et al. | 504/270 |
| 4,509,971 | 4/1985 | Forster et al. | 540/480 |
| 4,784,682 | 11/1988 | Forster et al. | 548/221 |
| 4,833,243 | 5/1989 | Forster et al. | 548/165 |
| 5,101,034 | 3/1992 | Schmidt | 548/136 |

FOREIGN PATENT DOCUMENTS

| | | |
|---|---|---|
| 0037526 | 3/1981 | European Pat. Off. |
| 0037938 | 3/1981 | European Pat. Off. |
| 0062254 | 3/1982 | European Pat. Off. |
| 3724467 | 7/1987 | Fed. Rep. of Germany |

OTHER PUBLICATIONS

Chemical Abstracts, vol. 96, 1982, Entry 68984m (1982).
Chemical Abstracts, vol. 96, 1982, Entry 52297d (1982).

Primary Examiner—Ronald G. Daus
Attorney, Agent, or Firm—Sprung Horn Kramer & Woods

[57] ABSTRACT

Herbicidal new 2-(2-benzoxazolyloxy)-acetamides of the formula

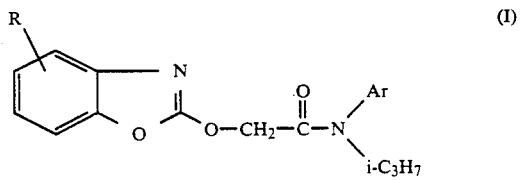

in which
R represents hydrogen, halogen, alkyl or halogenoalkyl and
Ar represents optionally substituted aryl, but with the exception of the compounds N-isopropyl-2-(2-benzoxazolyl-oxy)-acetanilide and N-isopropyl-2-(6-chlorobenzoxazol-2-yl-oxy)-acetanilide.

7 Claims, No Drawings

HERBICIDAL 2-(2-BENZOXAZOLYL-OXY)-ACETAMIDES

The invention relates to new 2-(2-benzoxazolyl-oxy)acetamides, to a process for their preparation, and to their use as herbicides.

It is known that certain 2-(2-benzoxazolyl-oxy)-acetamides such as, for example, the compound N-isopropyl 2-(6-chlorobenzoxazol-2-yl-oxy)-acetanilide, have herbicidal properties (cf., for example, DE-A 2,903,966; EP-A 5,501; U.S. Pat. No. 4,509,971; U.S. Pat. No. 4,833,243; DE-A 3,038,599; DE-A 3,038,652; DE-A 3,418,168; EP-A 161,602; U.S. Pat. No. 4,784,682; DE-A 3,724,467).

However, the herbicidal activity of these previously known compounds to problem weeds and their tolerance by important crop plants are not entirely satisfactory in all fields of application.

New 2-(2-benzoxazolyl-oxy)-acetamides of the general formula (I)

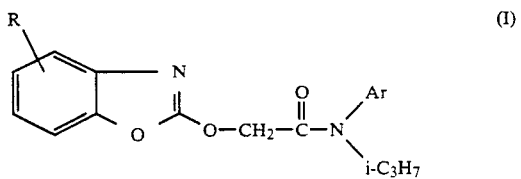

in which

R represents hydrogen, halogen, alkyl or halogenoalkyl and

Ar represents optionally substituted aryl, but with the exception of the compounds N-isopropyl-2-(2-benzoxazolyl-oxy)-acetanilide and N-isopropyl-2-(6-chlorobenzoxazol-2-yl-oxy)-acetanilide, have been found.

Furthermore, it has been found that the new 2-(2-benzoxazolyl-oxy)-acetamides of the general formula (I) are obtained when benzoxazole derivatives of the formula (II)

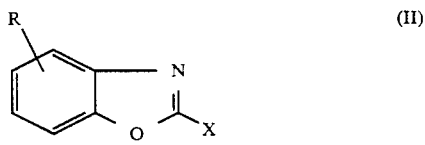

in which

X represents halogen or alkylsulphonyl and

R has the abovementioned meaning, are reacted with 2-hydroxyacetamides of the formula (III)

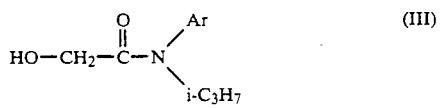

in which

Ar has the abovementioned meaning, if appropriate in the presence of a diluent and if appropriate in the presence of a reaction auxiliary.

Finally, it has been found that the new 2-(2-benzoxazolyl-oxy)-acetamides of the general formula (I) have herbicidal properties.

Surprisingly, the new 2-(2-benzoxazolyl-oxy)-acetamides of the general formula (I) according to the invention display a considerably better herbicidal activity against problem weeds compared with the known 2-(2-benzoxazolyloxy)-acetamides which are known from the prior art such as, for example, N-isopropyl 2-(6-chlorobenzoxazol-2-yl-oxy)-acetanilide, while having a similarly good tolerance by important crop plants.

Formula (I) provides a general definition of the new 2-(2-benzoxazolyl-oxy)-acetamides according to the invention. Preferred compounds of the formula (I) are those in which R represents hydrogen, fluorine, chlorine, bromine, iodine, straight-chain or branched alkyl having 1 to 8 carbon atoms or straight-chain or branched haloalkyl having 1 to 4 carbon atoms and 1 to 9 identical or different halogen atoms and Ar represents phenyl or naphthyl, each of which is optionally monosubstituted or polysubstituted by identical or different substituents, suitable substituents in each case being:

halogen, cyano, nitro, in each case straight-chain or branched alkyl, alkoxy or alkylthio, each of which has 1 to 6 carbon atoms, in each case straight-chain or branched halogenoalkyl, halogenoalkoxy or halogenoalkylthio, each of which has 1 to 6 carbon atoms and 1 to 13 identical or different halogen atoms, with the exception of the compounds N-isopropyl 2-(2-benzoxazolyl-oxy)-acetanilide and N-isopropyl 2-(6-chlorobenzoxazol-2-yl-oxy)-acetanilide.

Particularly preferred are compounds of the formula (I) in which

R represents hydrogen, fluorine, chlorine, bromine, straight-chain or branched alkyl having 1 to 6 carbon atoms or straight-chain or branched halogenoalkyl having 1 to 3 carbon atoms and 1 to 7 identical or different halogen atoms and Ar represents phenyl which is optionally monosubstituted to trisubstituted by identical or different substituents, suitable substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, with the exception of the compounds N-isopropyl 2-(2-benzoxazolyl-oxy)-acetanilide and N-isopropyl 2-(6-chlorobenzoxazol-2-yl-oxy)-acetanilide.

Very particularly preferred compounds of the formula (I) are those in which

R represents hydrogen, chlorine, methyl, ethyl, n- or i-propyl, n-, i-, s- or t-butyl or trifluoromethyl, and Ar represents phenyl which is optionally monosubstituted or disubstituted by identical or different substituents, suitable substituents being:

fluorine, chlorine, bromine, nitro, methyl, ethyl, n- or i-propyl, n-, i-, s- or t-butyl, methoxy, ethoxy, n- or i-propoxy, methylthio, trifluoromethyl, trifluoromethoxy and/or trifluoromethylthio, with the exception of the compounds N-isopropyl 2-(2-benzoxazolyl-oxy)-acetanilide and N-isopropyl 2-(6-chlorobenzoxazol-2-yl-oxy)-acetanilide.

Reference is made to the individual compounds mentioned in the Preparation Examples.

If, for example, 2-chloro-5-methylbenzoxazole and N-isopropyl 2-hydroxy-acetanilide are used as starting substances, the course of the reaction of the process according to the invention can be represented by the following equation:

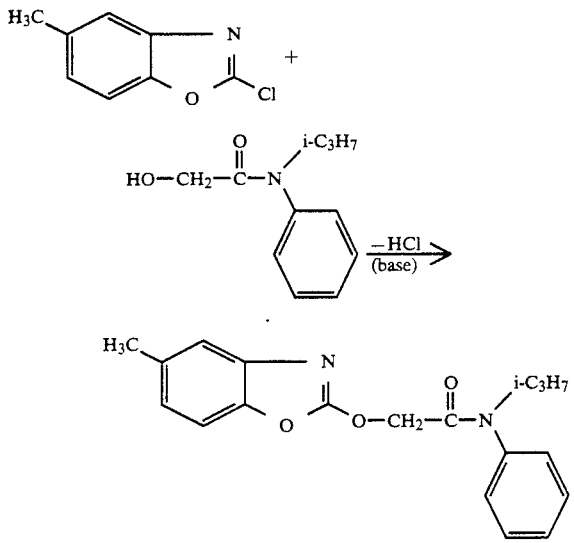

Formula (II) provides a general definition of the benzoxazole derivatives required as starting materials for carrying out the process according to the invention. In this formula (II), R preferably represents those radicals which have already been mentioned in connection with the description of the compounds of the formula (I) according to the invention as being preferred for this substituent.

X in formula (II) preferably represents fluorine, chlorine or bromine, or straight-chain or branched alkylsulphonyl having 1 to 4 carbon atoms, in particular chlorine or methylsulphonyl.

The benzoxazole derivatives of the formula (II) are known or can be obtained analogously to known processes (cf., for example, EP 141,053; EP 43,573; DE 3,025,910; Am. Chem. J. 21, 111 [1899]; J. Prakt. Chem. [2] 42, 445 (1890); DE 1,164,413).

Formula (III) provides a general definition of the 2-hydroxyacetamide furthermore required as starting materials for carrying out the process according to the invention. In this formula (III), Ar preferably represents those radicals which have already been mentioned in connection with the description of the compounds of the formula (I) according to the invention as being preferred for this substituent.

The 2-hydroxyacetamides of the formula (III) are also known (cf., for example, DE 3,821,600).

Suitable diluents for carrying out the process according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides such as dimethyl sulphoxide or alcohols such as methanol, ethanol, n- or i-propanol or n-, i-, s- or t-butanol.

The process according to the invention is preferably carried out in the presence of a suitable reaction auxiliary. Suitable reaction auxiliaries are all inorganic and organic bases which can customarily be used. The following are preferably used: the hydrides, hydroxides, amides, alcoholates, carbonates or hydrogen carbonates of alkali metals such as, for example, sodium hydride, sodium amide, sodium hydroxide, sodium methylate, sodium ethylate, potassium t-butylate, sodium carbonate or sodium hydrogen carbonate, or else tertiary amines such as, for example, triethylamine, N,N-dimethylaniline, pyridine, N,N-dimethylaminopyridine, diazabicyclooctane (DABCO), diazabicyclononene (DBN) or diazabicycloundecene (DBU).

When carrying out the process according to the invention, the reaction temperatures can be varied within a substantial range. In general, the process is carried out at temperatures between −40° C. and 120° C., preferably at temperatures between −20° C. and 60° C.

For carrying out the process according to the invention, 1.0 to 2.0 moles, preferably 1.0 to 1.5 moles, of 2-hydroxyacetamide of the formula (III) and, if appropriate, 0.1 to 2.0 moles, preferably 1.0 to 1.2 moles, of reaction auxiliaries are generally employed per mole of benzoxazole derivative of the formula (II).

The reaction is carried out and the reaction products are worked up and isolated by known processes (cf. in this context for example EP 348,734; EP 5,501; DE 3,821,600, or the Preparation Examples).

The end products of the formula (I) are purified with the aid of customary processes, for example by column chromatography or by recrystallisation. They are characterised with the aid of the melting point or, in the case of non-crystallising compounds, with the aid of the refractive index or the proton nuclear resonance spectroscopy ($^1$H-NMR).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

In this context, the active compound according to the invention can be employed with particularly good success for combating monocotyledon weeds in monocotyledon and dicotyledon cultures such as, for example, cotton or rice.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxaprop-ethyl, fluazifop-butyl, haloxyfopmethyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluoralin; diphenyl ethers such as, for example, acifluorfen, bifenox, fluoroglycofen, fomesafen, halosafen, lactofen and oxyfluorfen; ureas such as, for example, chlorotoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuronmethyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

Example 1

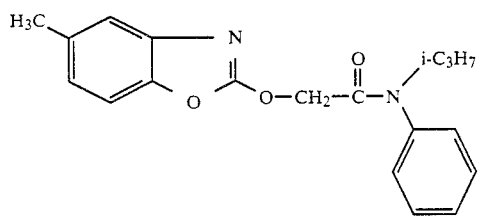

A solution of 2.4 g (0.06 mol) of sodium hydroxide in 10 ml of water is added dropwise with stirring at −20° C. to 9.8 g (0.05 mol) of N-isopropyl-hydroxyacetanilide and 7.6 g (0.045 mol) of 2-chloro-5-methyl-benzoxazole in 100 ml of acetone, and the mixture is then stirred for 3 hours at 0° to 5° C. For working up, water is added and the mixture is stirred until the product turns crystalline, and this is then filtered off with suction and dried.

13.6 g (85% of theory) of 2-(5-methyl-benzoxazol-2-yl-oxy)-N-isopropyl-acetanilide of melting point 108° C. are obtained.

The following 2-(2-benzoxazolyl-oxy)-acetamides of the general formula (I) are obtained in a corresponding manner and following the general preparation instructions:

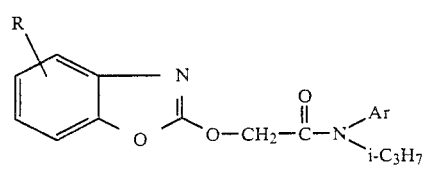

TABLE 1

| Example No. | (structure) | Ar | Melting point/°C |
|---|---|---|---|
| 2 | | 4-F-phenyl | 108 |
| 3 | | 3-F-phenyl | 116 |
| 4 | | 2-F-phenyl | 91 |
| 5 | | 3-Cl-phenyl | 115 |
| 6 | | 4-Cl-3-F-phenyl | 153 |
| 7 | | 2,4-Cl-phenyl | 107 |
| 8 | | 2-Cl-phenyl | 76 |
| 9 | | 3-CH₃-4-Cl-phenyl | 147 |
| 10 | | 4-OCH₃-phenyl | 128 |

TABLE 1-continued

| Example No. | R-benzoxazole | Ar | Melting point/°C |
|---|---|---|---|
| 11 | benzoxazole | 2-OCH₃-phenyl | 94 |
| 12 | benzoxazole | 4-OC₂H₅-phenyl | 85 |
| 13 | benzoxazole | 3-Cl-4-SCH₃-phenyl | 152 |
| 14 | benzoxazole | 3-Cl-4-OCH₃-phenyl | 97 |
| 15 | benzoxazole | 3,5-(CF₃)₂-phenyl | 132 |
| 16 | benzoxazole | 3-CH₃-phenyl | 100 |
| 17 | benzoxazole | 4-Cl-phenyl | 100 |
| 18 | benzoxazole | 4-CH₃-phenyl | 70 |
| 19 | benzoxazole | 2-CH₃-phenyl | 95 |
| 20 | benzoxazole | 2,5-(CH₃)₂-phenyl | 127 |
| 21 | benzoxazole | 2,4-(CH₃)₂-phenyl | 106 |
| 22 | benzoxazole | 3-CF₃-phenyl | 114 |
| 23 | benzoxazole | 2-Cl-3-CH₃-phenyl | 153 |
| 24 | 5-Cl-benzoxazole | phenyl | 115 |
| 25 | 5-CF₃-benzoxazole | phenyl | 88 |
| 26 | 5-CH₃-benzoxazole | 4-Cl-phenyl | 114 |
| 27 | 5-CH₃-benzoxazole | 3-Cl-phenyl | 88 |
| 28 | 5-CH₃-benzoxazole | 2-Cl-phenyl | 96 |
| 29 | 5-Cl-benzoxazole | 3-Cl-phenyl | 132 |
| 30 | 5-Cl-benzoxazole | 4-Cl-phenyl | 157 |

TABLE 1-continued

| Example No. | (structure with R) | Ar | Melting point/°C |
|---|---|---|---|
| 31 | 5-Cl benzoxazole, =N-C(CH3)= | 4-F-phenyl | 140 |
| 32 | 5-Cl benzoxazole, =N-C(CH3)= | 3-F-phenyl | 85 |
| 33 | 5-Cl benzoxazole, =N-C(CH3)= | 2-F-phenyl | 128 |
| 34 | 5-Cl benzoxazole, =N-C(CH3)= | 3-CH3-phenyl | 126 |
| 35 | 5-Cl benzoxazole, =N-C(CH3)= | 2-Cl-phenyl | 117 |
| 36 | 5-Cl benzoxazole, =N-C(CH3)= | 3-Cl-4-F-phenyl | 122 |
| 37 | 5-Cl benzoxazole, =N-C(CH3)= | 2,5-diF-phenyl | 105 |
| 38 | 5-Cl benzoxazole, =N-C(CH3)= | 2,4-diF-phenyl | 102 |
| 39 | 5-Cl benzoxazole, =N-C(CH3)= | 2,4-diCl-phenyl | 122 |
| 40 | 5-Cl benzoxazole, =N-C(CH3)= | 3-OCH3-phenyl | 88 |
| 41 | 5-Cl benzoxazole, =N-C(CH3)= | 4-Cl-phenyl | 223 |
| 42 | 5-Cl benzoxazole, =N-C(CH3)= | 3,5-diCH3-phenyl | 148 |
| 43 | 5-Cl benzoxazole, =N-C(CH3)= | 3-CH3-phenyl | 75 |
| 44 | 5-Cl benzoxazole, =N-C(CH3)= | 4-F-phenyl | 120 |
| 45 | 5-Cl benzoxazole, =N-C(CH3)= | 2-F-phenyl | 124 |
| 46 | 5-Cl benzoxazole, =N-C(CH3)= | 3-Cl-4-SCH3-phenyl | 130 |
| 47 | 5-Cl benzoxazole, =N-C(CH3)= | 3,4-diCl-phenyl | 102 |
| 48 | 5-Cl benzoxazole, =N-C(CH3)= | 3,5-diCl-phenyl | 129 |
| 49 | 5-Cl benzoxazole, =N-C(CH3)= | 4-OC2H5-phenyl | 75 |

TABLE 1-continued

| Example No. | Ar | Melting point/°C |
|---|---|---|
| 50 | 4-OCH₃-C₆H₄ | 112 |
| 51 | 3-F-C₆H₄ | 107 |
| 52 | 2-Cl-C₆H₄ | 101 |
| 53 | 3-Cl-C₆H₄ | 135 |
| 54 | 3-Cl-4-CH₃-C₆H₃ | 99 |
| 55 | 2-CH₃-4-Cl-C₆H₃ | 130 |
| 56 | 2-CH₃-4-CH₃-C₆H₃ | 104 |
| 57 | 4-CF₃-C₆H₄ | 121 |
| 58 | 4-CH₃-C₆H₄ | 132 |
| 59 | 3-CH₃-C₆H₄ | 135 |
| 60 | 2-OCH₃-C₆H₄ | 112 |
| 61 | 3,5-(CF₃)₂-C₆H₃ | 117 |

(All compounds have the 5-chlorobenzoxazol-2-yl ketimine core: Cl-C₆H₃-(N=C(CH₃))-O- linked to Ar)

USE EXAMPLES

In the Use Examples which follow, the compound listed below was employed as comparison substance:

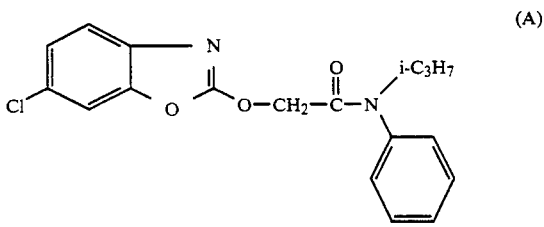

(A)

N-Isopropyl-2-(6-chlorobenzoxazol-2-yl-oxy)-acetanilide (cf., for example, DE 3,418,168; DE 3,724,467).

EXAMPLE A

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added, and the concentrate is diluted with water to the desired concentration.

Seeds of the test plants are sown in normal soil and, after 24 hours, watered with the preparation of active compound. It is expedient here to keep constant the amount of water per unit area. The concentration of active compound in the preparation is of no importance, only the amount of active compound applied per unit area being decisive. After three weeks, the degree of damage of plants is rated in % damage compared with the development of the untreated control. The figures denote:

0% = no action (like untreated control)
100% = total destruction

A clearly superior activity compared with the prior art is shown, in this test, for example by the compounds of the following Preparation Examples: 1, 2, 3, 5, 6, 7, 10, 12, 14, 16, 17, 18, 20, 22, 23, 26, 43, 44, 49, 51, 53, 54 and 58.

It will be appreciated that the instant specification and claims are set forth by way of illustration and not limitation, and that various modifications and changes may be made without departing from the spirit and scope of the present invention.

We claim:

1. A 2-(benzoxazolyl-oxy)-acetamide of the formula

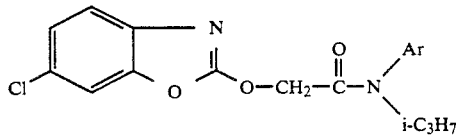

(I)

in which
Ar represents phenyl which is monosubstituted or disubstituted by identical or different substituents selected from the group consisting of fluorine, chlorine, methyl, methoxy, ethoxy, methylthio and trifluoromethyl.

2. A compound according to claim 1, wherein Ar is mono-methyl-phenyl or di-methyl-phenyl.

3. A compound according to claim 1, wherein Ar is substituted at least once by a substituent selected from the group consisting of fluorine, chlorine, methoxy, ethoxy, methylthio and trifluoromethyl.

4. A compound according to claim 1, wherein such compound is 2-(6-chloro-benzoxazol-2-yl-oxy)-N-isopropyl-N-(3-methyl-phenyl)-acetamide of the formula

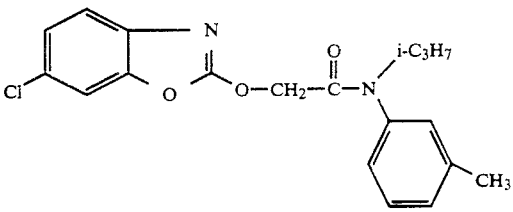

5. A herbicidal composition comprising a herbicidally effective amount of a compound according to claim 1 and a diluent.

6. A method of combating unwanted vegetation which comprises applying to such vegetation or to a locus from which it is desired to exclude such vegetation a herbicidally effective amount of a compound according to claim 1.

7. The method according to claim 6, wherein such compound is 2-(6-chloro-benzoxazol-2-yl-oxy)-N-isopropyl-N-(3-methyl-phenyl)-acetamide.

* * * * *